United States Patent [19]

Kuroda et al.

[11] Patent Number: 5,051,486

[45] Date of Patent: Sep. 24, 1991

[54] PREPARATION OF POLYMERS USEFUL AS POLYMERIC SOLID ELECTROLYTES AND COMPATIBILIZERS

[75] Inventors: Nobuyuki Kuroda; Hiroshi Kobayashi, both of Yokohama; Kazuo Matsuura, Tokyo, all of Japan

[73] Assignee: Nippon Oil Co., Ltd., Tokyo, Japan

[21] Appl. No.: 576,152

[22] Filed: Aug. 29, 1990

Related U.S. Application Data

[63] Continuation of Ser. No. 399,332, Aug. 28, 1989, abandoned, which is a continuation of Ser. No. 252,524, Oct. 3, 1988, abandoned.

[30] Foreign Application Priority Data

Oct. 7, 1987 [JP] Japan ............................ 62-251593

[51] Int. Cl.$^5$ ............................................. C08F 30/08
[52] U.S. Cl. .................................................. 526/279
[58] Field of Search ................. 526/279; 556/436, 465

[56] References Cited

PUBLICATIONS

Bazant et al., *Organosilicon Compounds*, Academic Press, New York, 1965, pp. 51–61.

*Primary Examiner*—Joseph L. Schofer
*Assistant Examiner*—Jeffrey T. Smith
*Attorney, Agent, or Firm*—Schmeiser, Morelle & Watts

[57] ABSTRACT

A macromer of the general formula (3) is prepared by a reaction between a silane compound of the general formula (1) and a polyethylene glycol monoalkyl ether of the general formula (2).

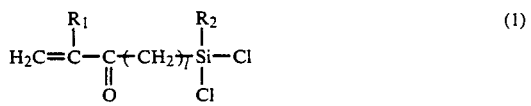

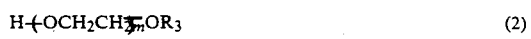

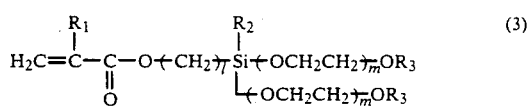

$R_1$: H, or $C_1$–$C_5$ alkyl group;
$R_2$: H, $C_1$–$C_5$ alkyl group, or $-(OCH_2CH_2)_p OR_4$;
$R_3$: $C_1$–$C_{10}$ alkyl;
$R_4$: $C_1$–$C_{10}$ alkyl;
l: integer of from 1 to 10 ($1 \leq l \leq 10$);
m: integer of from 1 to 30 ($1 \leq m \leq 30$); and
p: integer of from 1 to 30 ($1 \leq p \leq 30$).

6 Claims, No Drawings

5,051,486

PREPARATION OF POLYMERS USEFUL AS POLYMERIC SOLID ELECTROLYTES AND COMPATIBILIZERS

This application is a continuation of application Ser. No. 399,332, filed Aug. 28, 1989, which is a continuation of application Ser. No. 252,524, filed Oct. 3, 1988.

BACKGROUND OF THE INVENTION a) Field of the Invention

This invention relates to novel macromers containing at least one polyether moiety in at least one side chain thereof, a preparation process thereof and polymers thereof.

b) Description of the Related Art

As measures for developing functional high-molecular materials, it has recently been reported to obtain comb-like polymers by polymerizing a variety of macromers which are polymerizable monomers with at least one substituent group of a relatively high molecular weight containing one or more certain specific recurring units. Acrylic acid ester macromers, styrene macromers, vinyl ether macromers, oxazoline macromers, etc. have been proposed as such macromers. As acrylic acid ester macromers, may be mentioned by way of example methyl methacrylate macromers containing one or more $-(CH_2CH_2O)-$ moieties as recurring units [P. Masson et al., Polym. Bull., 7, 17 (1982)], methacrylic ester macromers containing one or more

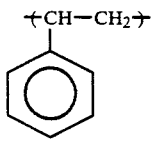

moieties as recurring units (U.S. Pat. No. 3,786,116), methyl methacrylate macromers containing one or more

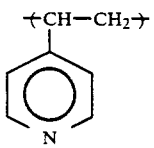

moieties as recurring units [P. Rempp et al., Makromol. Chem. Suppl., 8, 3 (1984)], methyl methacrylate macromers containing one or more

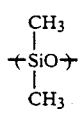

moieties as recurring units [Kawakami et al., Makromol. Chem., 185, 9 (1984)], and methyl methacrylate macromers containing one or more

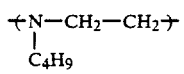

moieties as recurring units [E. J. Goethals et al., Polym. Bull., 4, 521 (1981)]. Macromers containing a variety of recurring units have also been proposed regarding styrene macromers, vinyl ether macromers and oxazoline macromers.

Comb-like polymers which are obtained by polymerizing such macromers as mentioned above are useful as matrixes for surface/interface modifying agents (for making surfaces hydrophobic or water-repellant, making interfaces hydrophilic, or improving the adhesion of surfaces), compatibilizers, high impact resins, adhesives, medical materials (antithrombotic), permeable membranes, age resisters, high molecular catalysts, and polymeric solid electrolytes. etc. in application fields such that both physical properties and function such as a micro-phase separation structure and amphiphilicity and interfacial activity are exhibited in combination.

SUMMARY OF THE INVENTION

An object of this invention is to provide novel macromers which can afford comb like polymers having many functions as described above.

In one aspect of this invention, there is thus provided a novel macromer containing at least one polyether moiety in a side chain thereof and represented by the following general formula:

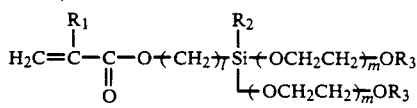

wherein $R_1$ is a hydrogen atom or an alkyl group having b 1-5 carbon atoms, $R_2$ is a hydrogen atom, an alkyl group having 1-5 carbon atoms of $-(OCH_2CH_2)_p OR_4$, p being an integer of from 1 to 30 ($1 \leq p \leq 30$) and $R_4$ being an alkyl group having 1-10 carbon atoms, $R_3$ is an alkyl group having 1-10 carbon atoms, l is an integer of from 1 to 10 ($1 \leq l \leq 10$), and m is an integer of from 1 to 30 ($1 \leq l \leq 30$).

The macromer according to this invention can provide novel comb-structure polymers containing one or more $-(CH_2CH_2O)-$ moieties as recurring units in side chains thereof by polymerization or copolymerization. Such comb-structure polymers can be used suitably as matrixes for compatibilizers and solid polymeric solid electrolytes, etc.

DESCRIPTION OF PREFERRED EMBODIMENTS

The macromer according to this invention can be obtained by reacting a silane compound represented by the following general formula:

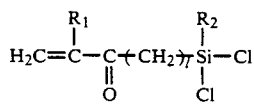

wherein $R_2$ have the same meaning as defined above $R_2$ or is a chlorine atom, with a polyethylene glycol monoalkyl ether represented by the following general formula:

In the above general formulae, $R_1$ is a hydrogen atom or an alkyl group having 1-5 carbon atoms with a hydrogen atom or an alkyl group having about 1-3 carbon atoms being preferred, $R_2$ is a hydrogen atom, an alkyl group having 1-5 carbon atoms or $-(OCH_2CH_2)_p OR_4$ with an alkyl group having 1-3 carbon atoms being preferred, and $R_3$ and $R_4$ are individually an alkyl group having 1-10 carbon atoms with an alkyl group having 1-3 carbon atoms being preferred. In addition, l is an integer of from 1 to 10 with 2, 3 or 4 being preferred, while m and p are individually an integer of from 1 to 30 with an integer of from 2 to 20 being preferred. Daringly describing a more preferable range, m and p are each an integer of from 7 to 15.

As silane compounds usable in the above reaction, may be mentioned 2-acryloxyethylmethyldichlorosilane, 2-methacryloxyethylmethyldichlorosilane, 2-methacryloxyethylpropyldichlorosilane, 3-acryloxypropylmethyldichlorosilane, 3-methacryloxypropylmethyldichlorosilane, 3-methacryloxypropyltrichlorosilane, 4-acryloxybutylmethyldichlorosilane, 4-methacryloxybutylmethyldichlorosilane, 5-methacryloxypentylmethyldichlorosilane, and mixtures thereof.

Illustrative examples of the polyethylene glycol monoalkyl ether includes polyethylene glycol monomethyl ether, polyethylene glycol monoethyl ether, polyethylene glycol monoisopropyl ether, polyethylene glycol mono-n-butyl ether, polyethylene glycol monoisobutyl ether, and mixtures thereof.

It is preferred to have an aromatic hydrocarbon such as benzene, toluene, xylene or a mixture thereof or an ether such as diethyl ether, isopropyl ether, n-butyl ether, tetrahydrofuran or a mixture thereof existed as a solvent upon reaction of the silane compound and polyethylene glycol monoalkyl ether. It is also desirable to have an amine such as pyridine or triethylamine coexisted so as to collect hydrogen chloride to be byproduced. Although the reaction temperature varies depending on the kinds of the silane compound and polyethylene glycol monoalkyl ether used, the solvent employed and the like, it is generally preferred to conduct the reaction under reflux of the solvent used. The reaction temperature may generally range from 0.5 to 40 hours with a range of 2-5 hours being preferred. Regarding the molar ratio of both reactants, the ratio of the silane compound to the polyethylene glycol monoalkyl ether may preferably range from 1:2 to 1:4.

A comb-like polymer containing a polyether chain in side chains thereof can be obtained by polymerizing the thus-obtained macromer in the presence of a conventional radical polymerization initiator, e.g., N,N'-azobisisobutyronitrile, benzoyl peroxide or the like in a solvent.

Illustrative examples of the solvent employed in the above polymerization include alcohols such as methanol, ethanol, isopropanol, n-butanol and mixtures thereof and ethers such as diethyl ether, isopropyl ether, tetrahydrofuran, dioxane and mixtures thereof. The polymerization temperature may range from 30° to 100° C. with a range of 40°-60° C. being preferred.

It is also possible to copolymerize the macromer of this invention with vinyl compounds which are polymerizable radically. As radically-polymerizable vinyl compounds, may be mentioned styrene, α-methylstyrene, methyl acrylate, methyl methacrylate, acrylonitrile and the like, and mixtures thereof.

This invention will hereinafter be described specifically by the following Examples. It should however be borne in mind that this invention is not necessarily limited to or by the following Examples.

EXAMPLE 1

<Synthesis of Macromer>

A nitrogen-purged 1-l three-neck flask equipped with a reflux condenser was charged with 200 ml of anhydrous benzene, 35 g (0.1 mole) of polyethylene glycol monomethyl ether (molecular weight: 350; m=9) and 15.8 g (0.2 mole) of anhydrous pyridine. After 12.1 g (0.05 mole) of 3-methacryloxypropylmethyldichlorosilane which had been dissolved in 20 ml of benzene was added dropwise at room temperature over 30 minutes, the resultant mixture was heated and reacted for 3 hours under reflux. After completion of the reaction, the reaction mixture was cooled to room temperature, filtered under nitrogen atmosphere and then processed through an alumina column. Benzene and pyridine were finally removed under reduced pressure to obtain 38.3 g of the target macromer Its yield was 89%.

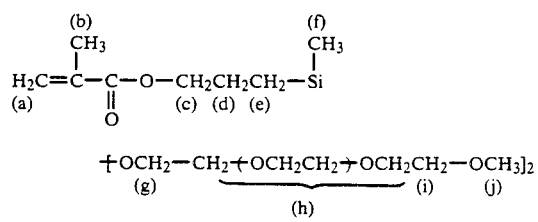

Its structural determination was conducted depending on proton nuclear magnetic resonance (in $CDCl_3$; internal standard: TMS ppm).

Proton (a): 5.3-6.3 ppm
Proton (b): 1.94 ppm
Proton (c): 4.2 ppm
Proton (d): 1.95 ppm
Proton (e): 0.7 ppm
Proton (f): 0.12 ppm
Protoh (g): 3.85 ppm
Proton (h): 3.55 ppm
Proton (i): 3.45 ppm
Proton (j): 3.23 ppm
(e):(g)=1:2.03 (1:2, calculated)
{(b)+(c)+(d)+(f)}:(j)=10:6.05 (10:6, calculated)

<Polymerization of Macromer>

Methanol was added to 8.6 g (about 10 mmol) of the macromer synthesized above to give a final volume of 20 ml followed by dissolution of 40 mg (0.243 mmol) of N,N'-azobisisobutyronitrile. The resultant solution was then injected by a syringe into a 100-ml glass ampule which was fitted with a three-way cock and had been purged with nitrogen in advance. The solution was frozen with liquefied nitrogen, deaerated and molten. This procedure was repeated three times. The solution was then frozen and sealed under high vacuum. The solution was allowed to undergo a reaction at 60° C. for 6 days after the sealing.

After the lapse of the predetermined time, the ampule was opened and its contents were poured into a large volume of diethyl ether to purify a polymer thus produced. The polymer was lyophilized from benzene. Its yield was 4.7 g. Its number average molecular weight was found to be 10,200 by a vapor pressure osmometer.

EXAMPLES 2-5

Macromers containing a polyether moiety in side chains thereof were synthesized by separately using various compounds, which are shown in the following table, as silane compounds and polyethylene glycol monoalkyl ethers.

| | Silane compound* $$H_2C=\underset{R_1}{\overset{\phantom{|}}{C}}-\underset{\parallel}{C}-(CH_2)_l-\underset{\underset{Cl}{|}}{\overset{R_2}{Si}}-Cl$$ | | | Polyethylene glycol monoalkyl ether $H-(OCH_2CH_2)_m-OR_3$ | | Novel macromer $$H_2C=\underset{R_1}{\overset{\phantom{|}}{C}}-\underset{\parallel}{C}-O-(CH_2)_l-\underset{}{\overset{R_2}{Si}}\begin{array}{l}-(OCH_2CH_2)_m-OR_3\\ -(OCH_2CH_2)_m-OR_3\end{array}$$ | | | | |
|---------|-----|-----|---|---|----------|-----|-----|-----|---|----|
| Example | $R_1$ | $R_2$ | $l$ | $m$ | $R_3$ | $R_1$ | $R_2$ | $R_3$ | $l$ | $m$ |
| 2 | $CH_3$ | $CH_3$ | 2 | 7 | $CH_3$ | $CH_3$ | $CH_3$ | $CH_3$ | 2 | 7 |
| 3 | $CH_3$ | $CH_3$ | 4 | 9 | $CH_3$ | $CH_3$ | $CH_3$ | $CH_3$ | 4 | 9 |
| 4 | H | $CH_3$ | 3 | 9 | $CH_3$ | H | $CH_3$ | $CH_3$ | 3 | 9 |
| 5 | $CH_3$ | $i\text{-}C_3H_7$ | 3 | 15 | $i\text{-}C_3H_7$ | $CH_3$ | $i\text{-}C_3H_7$ | $i\text{-}C_3H_7$ | 3 | 15 |

*Example 2: 2-methacryloxyethylmethyldichlorosilane
Example 3: 4-methacryloxybutylmethyldichlorosilane
Example 4: 3-acryloxypropylmethyldichlorosilane
Example 5: 3-methacryloxypropylisopropyldichlorosilane

We claim:

1. In the making of a uncross-linked comb-like graft polymer uesful for compatibilizers or polymeric solid electrolytes, the process comprising:
   (a) dissolving in an organic solvent a macromer having a polyether moiety in a side chain thereof, the macromer being of general form:

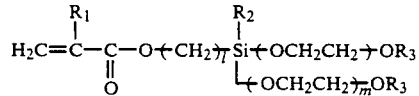

where, $R_1$ is H, or an alkyl group of 1-5 carbon atoms,
   $R_2$ is $R_1$ or $-(OCH_2CH_2)_p-OR_4$, p being an integer from 1 to 30,
   $R_3$ and $R_4$ being alkyl groups having 1-10 carbon atoms each,
   $l$ is an integer from 1-10, and
   $m$ is an integer from 1-30; and
   (b) initiating polymerization of the step (a) macromer by reacting it slowly in the absence of oxygen with a conventional radical polymerization initiator to obtain said polymer.

2. The process recited in claim 1 further comprising purifying said polymer by washing in an organic solvent and by lyophilizing it from aryl residuals.

3. The process recited in claim 2 wherein said reacting step is accomplished using a conventional radical polymerization initiator such as benzoyl peroxide or N,N'-azobisisobutyronitrile.

4. The process recited in claim 1 including a preliminary step of preparing the macromer by slowly mixing a silane compound with a polyethylene glycol monoalkyl ether; and, subsequently reacting the silane compound and the monoalkyl ether slowly by refluxing in order to obtain in the macromer at least one side chain containing therein at least one polyether moiety.

5. A method for making a polymer by initiating polymerization of a macromer of claim 1, the macromer containing at least one polyether moiety in at least one side chain thereof in order for said polymer to acquire comb-like and polyether side chain morphology, said initiating step further comprising reacting the macromer slowly with a radical polymerization initiator such as benzoyl peroxide or N,N'-azobisisobutyronitrile and subsequently purifying and isolating said polymer.

6. The process recited in claim 5 including the preliminary step of preparing the macromer by way of slow mixing of a silane compound with a polyethylene glycol monoalkyl ether; and, subsequently, slowly reacting the silane compound and the monoalkyl ether by refluxing in order to obtain in a side chain of the macromer at least one polyether moiety.

* * * * *